US00PP18827P3

(12) United States Plant Patent
Hofmann

(10) Patent No.: US PP18,827 P3
(45) Date of Patent: May 20, 2008

(54) *NEW GUINEA IMPATIENS* PLANT NAMED 'FISNICS MANG'

(50) Latin Name: *Impatiens hawken W. Bull*
Varietal Denomination: Fisnics Mang

(75) Inventor: Birgit Christa Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 199 days.

(21) Appl. No.: 11/330,441

(22) Filed: Jan. 12, 2006

(65) Prior Publication Data

US 2007/0163021 P1 Jul. 12, 2007

(51) Int. Cl.
*A01H 5/00* (2006.01)

(52) U.S. Cl. ..... Plt./318

(58) Field of Classification Search ..... Plt./318
See application file for complete search history.

(56) References Cited

U.S. PATENT DOCUMENTS

2007/0163021 P1 * 7/2007 Hofmann ..... Plt./318

OTHER PUBLICATIONS

PBR 04–2164 filed Oct. 13, 2004 published Nov. 30, 2004.*

* cited by examiner

*Primary Examiner*—Anne Marie Grunberg
*Assistant Examiner*—Georgia Helmer
(74) *Attorney, Agent, or Firm*—Jondle & Associates, P.C.

(57) ABSTRACT

A new New Guinea *Impatiens* plant particularly distinguished by medium sized carmine-pink to orange flowers with weak orange-red stripes and a deep red eye, on long deep purple pedicles, that are borne well above the foliage, early to medium flowering, medium green foliage with narrow leaves, and a medium plant habit that is round and bushy, is disclosed.

1 Drawing Sheet

Genus and species: *Impatiens hawkeri* W. Bull.
Variety denomination: 'Fisnics Mang'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Mang'. The new cultivar originated from a hybridization made in the year 2001 in Hillscheid, Germany. The female parent was the proprietary New Guinea *Impatiens* plant 'K98-4178-19' (unpatented), while the male parent was the New Guinea *Impatiens* plant 'Cabuya' (patent status unknown). The seeds produced by the hybridization were sown in November 2001 in Galdar, Gran Canaria, Spain. A single plant selection was chosen for further evaluation and for asexual propagation in April 2002 in Galdar, Gran Canaria, Spain.

The new cultivar was created in 2001 in Hillscheid, Germany and has been asexually reproduced repeatedly by vegetative cuttings and tissue culture in Galdar, Gran Canaria, Spain and Hillscheid, Germany, over a two-year period. 'Fisnics Mang' has not been observed under all possible environmental conditions. The present invention has been found to retain its distinctive characteristics through successive asexual propagations.

Plant Breeder's Rights for this cultivar were applied for in Switzerland on Oct. 13, 2004 and in Canada on Apr. 20, 2005.

SUMMARY OF THE INVENTION

The following are the most outstanding and distinguishing characteristics of this new cultivar when grown under normal horticultural practices in Hillscheid, Germany and Langley, British Columbia, Canada.

1. Carmine-pink to orange colored flowers, with weak, orange-red stripes, and with a deep red eye;
2. Medium sized flowers on long, deep purple pedicles, well above the foliage;
3. Medium green foliage and relatively narrow leaves;
4. A medium, round and bushy plant habit; and
5. An early to medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 13-weeks old, grown in a greenhouse in Hillscheid, Germany, in late Spring.

DESCRIPTION OF THE NEW CULTIVAR

The following detailed descriptions set forth the distinctive characteristics of 'Fisnics Mang'. The data which define these characteristics were collected from asexual reproductions carried out in Hillscheid, Germany. The plant history was taken on 12-week old plants which were planted as rooted cuttings in 12-cm pots in late February 2004, and then grown in a greenhouse at a minimum temperature of 16° C. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:

*Family.*—Balsaminaceae.

*Botanical.*—*Impatiens hawkeri* W. Bull.

*Common name.*—New Guinea *Impatiens.*

Parentage:

*Female parent.*—'K98-4178-19' a proprietary deep-salmon flowered New Guinea *Impatiens* plant (unpatented).

*Male parent.*—'Cabuya', a salmon-pink flowered New Guinea *Impatiens* plant (patent status unknown).

Growth:

*Growth and branching habit.*—Medium size, round, bushy, and well-branched; the growth is indeterminate, though weak after the beginning of flowering.

*Height.*—14.5 cm.

*Width.*—28.8 cm.

*Propagation.*—Terminal tips for cuttings.

*Time to produce a finished flowering plant.*—9 to 10 weeks for a 12-cm pot.

*Time to initiate and develop roots.*—18 days at 22° C.

Branches:

*Average number.*—10 to 15.

*Length of branches.*—12 cm to 14 cm.

*Internode length.*—3.5 cm to 4.5 cm.

*Diameter of branches.*—0.5 cm to 0.7 cm.

*Stem color.*—RHS 185A (dark red-purple).

Leaves:

*Arrangement.*—Primarily in whorls.

*Size.*—Length: 12.3 cm. Width: 4.4 cm.

*Shape.*—Elliptic.

*Margin.*—Slightly serrate, ciliated.

*Apex.*—Acuminate.

*Base.*—Acute.

*Color* (*mature leaves*).—Upper surface: Near RHS 137A (medium-green). Lower surface: RHS 138B (light-green).

*Color* (*immature leaves*).—Upper surface: RHS 137D (medium-green). Lower surface: RHS 138B (light-green).

*Texture.*—Surface is slightly glossy and smooth or faintly rippled.

*Venation color.*—Upper surface: RHS 48B. Lower surface: RHS 185B.

*Variegation.*—None.

*Petioles.*—Length: 2.3 cm. Diameter: 0.3 cm to 0.4 cm. Color: Upper surface: RHS 185A. Lower surface: RHS 185A. Texture: Glabrous.

Flower buds:

*Shape.*—Ovoid.

*Size.*—Length: 2.2 cm. Diameter: 1.5 cm.

*Color.*—Ranging from RHS 55A to RHS 52B.

Inflorescence:

*Blooming habit.*—9 to 10 weeks after planting of rooted cuttings.

*Inflorescence type.*—Flowers appear solitary on peduncles emerging from the leaf axils at the upper nodes of the stems.

*Number of flowers per node.*—7 to 9, in various stages of development.

*Flowering season.*—Mainly from March to October, depending on light intensity.

*Lastingness of individual blooms.*—Up to 14 days (in a greenhouse in the Spring at 18° C.).

*Peduncle.*—Color: RHS 183C (brownish-red). Size: Length: 5.5 cm. Diameter: 0.15 cm. Texture: Flexible, glabrous.

Flowers:

*Form of corolla.*—Zygomorphic, single-type, 5 petals.

*Shape of corolla.*—Nearly round, with the petals partly overlapping, the banner petal somewhat cup-shaped.

*Corolla size.*—Length: 7.5 cm. Width: 7.2 cm. Depth: 1.2 cm.

*Calyx.*—General: Composed of 3 sepals. Sepals: Shape: Two sepals are oval-shaped while the third is transformed into the spur. Color: RHS 147C (dull greenish). Length: 1.0 cm.

Petals:

*Shape.*—Cordate, weakly lobed at the top ends, the top petal slightly cupped.

*Apex.*—Retuse or emarginate.

*Base.*—Attenuate.

*Margin.*—Entire.

*Petal size.*—Top: Length: 3.1 cm. Width: 5.8 cm. Lateral: Length: 3.3 cm. Width: 3.7 cm. Lower: Length: 3.3 cm. Width: 4.1 cm.

*Color.*—General color description: Carmine pink with an orange hue in parts, and with weak orange-red stripes and a distinct deep red eye. Upper surface: RHS 55A, near margins of petals RHS 40C, with weak radial stripes RHS 44A to RHS 44B. Lower surface: RHS 52B to RHS 52C. Eye Zone: RHS 66A (red-purple), most distinct at the base of lateral petals.

*Petal texture.*—Smooth, silky.

*Aspect.*—Flat, banner petal may be somewhat cupped.

Spur:

*Shape.*—Downwardly curved.

*Color.*—RHS 53A to RHS 53B (deep red).

*Size.*—Length: 6.7 cm. Diameter: 0.3 cm (at the flower end).

Reproductive organs:

*Stamens.*—Number: 5 fused. Stamen color (upper surface color): RHS 46C. Anthers: Fused, hooded. Pollen color: RHS 8D (whitish-yellow).

*Pistils.*—Style and stigma: 5, very short, RHS 150D (pale-yellow). Ovary: 5-celled. Ovary length: 0.5 cm. Ovary color: RHS 141C (surface green).

Fruit and seed set: No seed set observed.

Disease and insect resistance: No particular resistance or susceptibility has been observed.

COMPARISON WITH PARENTAL AND COMMERCIAL CULTIVARS

'Fisnics Mang' differs from the female parent 'K98-4178-9' (unpatented) by having a somewhat fuller plant habit and uniform green foliage, while 'K98-4178-9' has leaves that tend to develop slight variegation.

'Fisnics Mang' differs from the male parent 'Cabuya' (patent status unknown), by having pink to salmon-orange colored flowers with orange stripes while 'Cabuya' has a more uniform colored pink flower with red eyes.

'Fisnics Mang' differs from the commercial cultivar 'Kimali' (U.S. Plant Pat. No. 14,033) by having larger flowers (larger diameter by 0.5 cm) that are somewhat less orange and more pink, and a taller plant habit (14.5 cm in contrast to 11.5 cm). Additionally, 'Kimali' develops more branches and has shorter leaves than 'Fisnics Mang'.

'Fisnics Mang' differs from cultivar 'Fisco Deepsalm' (U.S. Plant Pat. No. 17,586) by having a more pink and less orange flower color than 'Fisco Deepsalm'. Additionally, 'Fisnics Mang' has a taller plant habit (14.5 cm) and wider leaves (4.4 cm) than 'Fisco Deepsalm' (plant height is 9.7 cm and leaf width is 4.3 cm).

I claim:

1. A new and distinct cultivar of New Guinea *Impatiens* plant as shown and described herein.

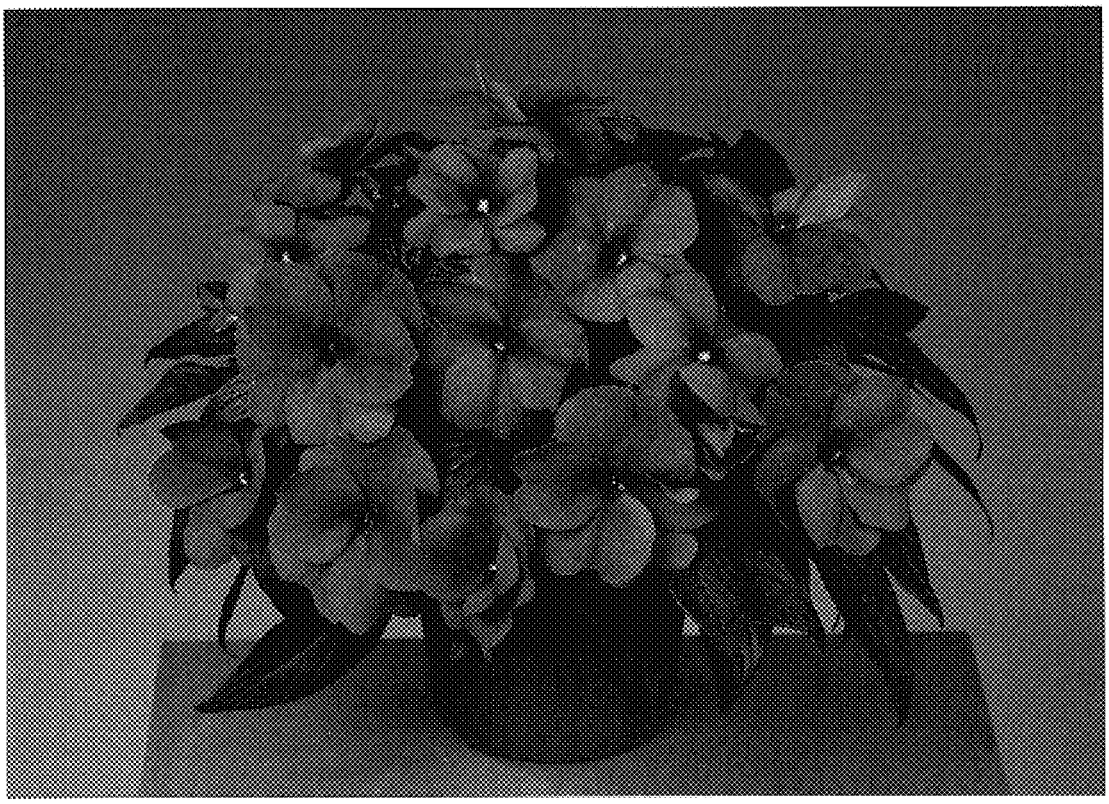

* * * * *